United States Patent [19]
Saum et al.

[11] Patent Number: 6,017,975
[45] Date of Patent: Jan. 25, 2000

[54] PROCESS FOR MEDICAL IMPLANT OF CROSS-LINKED ULTRAHIGH MOLECULAR WEIGHT POLYETHYLENE HAVING IMPROVED BALANCE OF WEAR PROPERTIES AND OXIDATION RESISTANCE

[76] Inventors: Kenneth Ashley Saum, 203 Wilson Rd., Newark, Del. 19711; William Michael Sanford, 52 Fawn La., Kennett Square, Pa. 19348; William Gerald Dimaio, Jr., 1306 Longmeadow Rd., Boothwyn, Pa. 19061; Edward George Howard, Jr., 844 Old Public Rd., Hockessin, Del. 19707

[21] Appl. No.: 08/911,792

[22] Filed: Aug. 15, 1997

Related U.S. Application Data

[60] Provisional application No. 60/027,354, Oct. 2, 1996.

[51] Int. Cl.$^7$ .......................................................... C08J 3/28
[52] U.S. Cl. .......................... 522/161; 522/184; 522/189; 522/911; 522/912; 528/503
[58] Field of Search ............................... 528/503; 522/65, 522/71, 161, 189, 184, 911, 912

[56] References Cited

U.S. PATENT DOCUMENTS

| | | |
|---|---|---|
| 5,414,049 | 5/1995 | Sun et al. ............................... 525/333.7 |
| 5,449,745 | 9/1995 | Sun et al. . |
| 5,543,471 | 8/1996 | Sun et al. . |

FOREIGN PATENT DOCUMENTS

| | | |
|---|---|---|
| 0 169 259 | 7/1984 | European Pat. Off. . |
| 0 722 973 A1 | 7/1996 | European Pat. Off. . |
| 0 729 981 A1 | 9/1996 | European Pat. Off. . |
| 09122222 | 5/1997 | Japan . |
| WO96/09330 | 3/1996 | WIPO . |
| WO97/29793 | 8/1997 | WIPO . |

OTHER PUBLICATIONS

Streicher, "Ionizing irradiation for sterilization and modification of high molecular weight polyethylenes", Plastics and Rubber Processing and Applications, vol. 10, No. 4, pp. 221–229, 1988.

Streicher, "Influence of Ionizing Irradiation in Air and Nitrogen for Sterilization of Surgical Grade Polyethylene for Implants", Radiat. Phys. Chem, vol. 31, Nos. 4–6, pp. 693–698, 1988.

Roe et al., "Effect of radiation sterilization and aging on ultrahigh molecular weight polyethylene", Journal of Biomedical Materials Research, vol. 15, pp. 209–230, 1981.

Kurth et al., "Effect of radiation Sterilization on UHMW–Polyethylene", Third World Biomaterials Congress, p. 589, Apr. 21–25, 1988.

Plessis et al., "The Improvement of Polyethylene Prostheses Through Radiation Crosslinking", Radiat. Phys. Chem., vol. 9, pp. 647–652, 1977.

Streicher, "The Behavior of UHMW–PE when Subjected to Sterilization by Ionizing Radiation", Ultra–High, Molecular Weight Polyethylene as Biomaterial in Orthopedic Surgery, pp. 66–73, 1990.

Grobbelaar et al., "The Radiation Improvement of Polyethylene Prostheses", The Journal of Bone and Joint Surgery, vol. 60–B, No. 3, pp. 370–374, Aug. 1978.

*Primary Examiner*—Duc Truong

[57] ABSTRACT

A medical implant of ultrahigh molecular weight polyethylene having an improved balance of wear properties and oxidation resistance is prepared by irradiating a preform of ultrahigh molecular weight polyethylene, annealing the irradiated preform in the absence of oxygen to a temperature at or above the onset of melting temperature, and forming an implant from the stabilized cross-linked polymer. Implants prepared according to the process of the present invention have comparable oxidation resistance and superior wear performance compared to unirradiated ultrahigh molecular weight polyethylene.

38 Claims, No Drawings

PROCESS FOR MEDICAL IMPLANT OF CROSS-LINKED ULTRAHIGH MOLECULAR WEIGHT POLYETHYLENE HAVING IMPROVED BALANCE OF WEAR PROPERTIES AND OXIDATION RESISTANCE

This application claims benefit of provisional application Ser. No. 60/027,354 filed Oct. 2, 1996.

BACKGROUND OF INVENTION

1. Field of Invention

This invention relates to a process for forming medical implants of cross-linked ultrahigh molecular weight polyethylene having an improved balance of wear properties and oxidation resistance.

2. Description of Related Art

It is known in the art that ultrahigh molecular weight polyethylene (UHMWPE) can be cross-linked by irradiation with high energy radiation, for example gamma radiation, in an inert atmosphere or vacuum. Exposure of UHMWPE to gamma irradiation induces a number of free-radical reactions in the polymer. One of these is cross-linking. This cross-linking creates a 3-dimensional network in the polymer which renders it more resistant to adhesive wear in multiple directions. The free radicals formed upon irradiation of UHMWPE can also participate in oxidation which reduces the molecular weight of the polymer via chain scission, leading to degradation of physical properties, embrittlement and a significant increase in wear rate. The free radicals are very long-lived (greater than eight years), so that oxidation continues over a very long period of time resulting in as much as a 5-fold increase in the wear rate as a result of oxidation over a period of about 5 years. As such, the wear rate of traditionally irradiated materials is significantly greater than unirradiated materials.

Sun et al. U.S. Pat. No. 5,414,049, which patent is hereby incorporated by reference, discloses a process for improving the oxidation resistance of medical implants which have been sterilized with radiation. In a preferred embodiment, a raw polymeric material is obtained by forming a virgin resin powder from which air and moisture have been removed prior to the forming process. The forming process, e.g. ram extrusion or compression molding of the powder is also preferably carried out in an inert low oxygen atmosphere. A medical implant is formed from the raw material, e.g. an olefinic material such as UHMWPE, and is sealed in an oxygen impermeable package in an oxygen reduced non-reactive atmosphere and radiation sterilized, followed by heating the sterilized packaged implant at a temperature of between 37° C. and the melting point of the olefinic material. The heating step forms cross-links between remaining free radicals formed during the radiation sterilization step, thus improving the oxidation resistance of the material. If the annealing temperature is too high, the thermal treatment can cause distortion of the UHMWPE implant, which is undesirable in orthopedic end-uses where the implants are generally machined or molded to close tolerances. If the temperature profile during annealing is adjusted to lower temperatures to avoid distortion of UHMWPE implants, incomplete extinguishing of the free radicals generally occurs and the UHMWPE oxidizes upon exposure to air or moisture.

Hyun et al. published International Application WO 96/09330, which application is hereby incorporated by reference, discloses a process for forming oriented UHMWPE materials for use in artificial joints by irradiating with low doses of high-energy radiation in an inert gas or vacuum to cross-link the material to a low degree, heating the irradiated material to a temperature at which compressive deformation is possible, preferably to a temperature near the melting point or higher, and performing compressive deformation followed by cooling and solidifying the material. The oriented UHMWPE materials have improved wear resistance. Medical implants may be machined from the oriented materials or molded directly during the compressive deformation step. The anisotropic nature of the oriented materials may render them susceptible to deformation after machining into implants.

Salovey et al. published European Application EP 722973, which application is hereby incorporated by reference, discloses a method for enhancing the wear-resistance of polymers, including UHMV/PE, by crosslinking them via irradiation in the melt or using peroxide or similar chemical agents.

The process of the present invention eliminates the problem of thermal distortion of the implant by irradiating and thermally treating a consolidated UHMWPE material prior to forming an implant therefrom. By separating the irradiation cross-linking step from the sterilization step, the current invention allows one to use lower levels of radiation for cross-linking than would be effective for sterilization of UHN wPD Additionally, the he treatment step following irradiation may be performed at temperatures near or above the melting point, which would distort the shape of a machined or molded inplant which has been packaged for final sterilization. Heat treatment near or above the melting point results in improved molecular mobility, elimination of free radicals in the crystalline regions of the polymer which cannot occur at temperatures below the melt, and increased cross-linking and reduced oxidation in aged samples. When heat treatment is carried out at lower temperatures, incomplete quenching of free radicals results in residual oxidation upon aging. By separating the irradiating and annealing steps, the process of the current invention also avoids the need to irradiate in the melt, which is difficult to achieve on a commercial scale. An additional object of the current invention is to prepare a medical implant of cross-linked UHMWPE having improved wear properties without the use of chemical cross-linking agents. Medical implants formed from the cross-linked UHMWPE material of the current invention may be packaged in an air-permeable package and sterilized using non-irradiative methods such as gas plasma or ethylene oxide, eliminating the need to package the implants in an inert atmosphere. The cross-linked UHMWPE of the current invention can also be used in nonmedical applications requiring high wear resistance.

SUMMARY OF THE INVENTION

The current invention pertains to a process for preparing cross-linked ultrahigh molecular weight polyethylene useful in medical implants. The process involves irradiating a preform of ultrahigh molecular weight polyethylene, preferably with gamma radiation. Optionally, the preform may be annealed prior to irradiation in an inert atmosphere without the application of external pressure. The irradiated preform is then annealed in a substantially oxygen free atmosphere at a temperature at or above the onset of melting temperature, preferably near or above the peak DSC melting point, for a sufficient time to substantially recombine (eliminate) all the free radicals and crosslink the ultrahigh molecular weight polyethylene. This annealing step may be done under isostatic or hydrostatic pressure. The annealed preform is cooled while maintaining the oxygen free atmosphere and formed into a medical implant. The implant is sterilized using non-irradiative methods. Sterilization preferably is done by packaging the implant in an air permeable package and treating with gas plasma.

The invention further pertains to an improved cross-linked ultrahigh molecular weight polyethylene that can be made by the process of this invention. This cross-linked ultrahigh molecular weight polyethylene preferably has a swell ratio of less than about 5 and oxidation level of less than about 0.2 carbonyl area/mil sample thickness after aging under an oxygen pressure of about 5 atmospheres. It preferably has a percent elongation at break of at least 250, a single notch IZOD strength of at least 15 foot pounds per inch (ft lb/in) of notch, and a double notch IZOD strength of at least 35 ft lb/sq. in. The medical implant of this cross-linked ultrahigh molecular weight polyethylene exhibits an improved balance of wear properties and oxidation resistance. Wear properties are superior to those of conventional ultrahigh molecular weight polyethylene sterilized using gas plasma or gamma-irradiation. Oxidative resistance is significantly improved over conventional gamma-sterilized ultrahigh molecular weight polyethylene and is comparable to unirradiated, gas plasma sterilized ultrahigh molecular weight polyethylene.

DETAILED DESCRIPTION

For the purposes of this invention ultrahigh molecular weight polyethylene is defined as a polyethylene having an estimated weight average molecular weight in excess of about 400,000, usually 1,000,000 to 10,000,000 as defined by a melt index (ASTM D-1238) of essentially zero and a reduced specific viscosity greater than 8, preferably 25–30.

An UHMWPE preform is used as the starting material in the current process. The term preform is used herein to refer to a shaped article which has been consolidated, such as by ram extrusion or compression molding of UHMWPE resin particles into rods, sheets, blocks, slabs or the like. Such preforms may be obtained or machined from commercially available UHMWPE, for example GUR 4150 HP ram extruded UHMWPE rods from PolyHi Solidur (Fort Wayne, Ind.). The starting preform may also be pressure recrystallized as described in Howard U.S. Pat. 5,478,906, which patent is hereby incorporated by reference. The UHMWPE preform material does not contain stabilizers, antioxidants, or other chemical additives which may have potential adverse effects in medical applications.

The process of the current invention includes the steps of irradiating a UHMWPE preform to form free radicals and cross-link the UHMWPE, annealing the irradiated UHMWPE preform at elevated temperature in a substantially oxygen free atmosphere to eliminate any free radicals remaining from the irradiation step, thus further cross-linking and increasing the oxidation resistance of the irradiated UHMWPE, and forming a medical implant from the annealed cross-linked preform. Gamma radiation is preferably used in the irradiation step, however electron beam or x-ray radiation may also be used. Ultrahigh molecular weight polyethylene prepared according to the process of the current invention has an improved balance of wear properties and oxidation resistance. The increased cross-linking results in reduced swell ratios, generally less than about 5, and improved wear performance with comparable oxidation resistance relative to unirradiated UHMWPE.

The preform is preferably irradiated in the solid state with gamma radiation at a dose of about 0.5–10 Mrad using methods known in the art. Preferably, the preform is irradiated at a dose of about 1.5–6 Mrad. Radiation doses of less than about 0.5 Mrad generally provide insufficient cross-linking to provide the desired increase in wear properties in the final implant. While doses of greater than 10 Mrad may be used, generally the additional improvement in wear properties that is achieved by the higher dose is offset by increasing brittleness of the UHMWPE due to higher levels of cross-linking. Ultrahigh molecular weight polyethylene prepared using the process of the current invention generally has a percent elongation at break of at least about 250, single notch Izod strength of at least about 15 ft lb/in of notch, preferably at least about 17 ft lb/in of notch, and double notch Izod strength of at least about 35 ft lb/sq in. UHMWPE which has been pre-annealed or annealed at temperatures greater than about 280° C. generally have a percent elongation at break of at least about 400, preferably at least about 500. The irradiation step is generally performed at room temperature, however higher temperatures may be used.

The preform is optionally contained in an inert atmosphere or vacuum, such as in an oxygen impermeable package during the irradiation step. Inert gases such as nitrogen, argon, and helium may be used. If a vacuum is used, the packaged material may be subjected to one or more cycles of flushing with an inert gas and applying a vacuum to eliminate oxygen from the package. Examples of packaging materials include metal foil pouches such as aluminum or MYLAR® polyester coated packaging foil which is available commercially for heat-sealed vacuum packaging. Polymeric packaging materials such as polyethylene terephthalate and poly(ethylene vinyl alcohol), both of which are commercially available may also be used. Irradiating the preform in an inert atmosphere reduces the effect of oxidation and accompanying chain scission reactions which can occur during gamma-irradiation. Oxidation that is caused by oxygen which is present in the atmosphere during irradiation is generally limited to the surface of the preform. Since the process of the current invention radiation cross-links the UHMWPE prior to forming the implant, low levels of surface oxidation can be tolerated as the oxidized surface can be removed during subsequent machining of the implant from the preform.

After the UHMWPE preform has been gamma irradiated, it is heat treated by holding at elevated temperature in a substantially oxygen-free atmosphere, typically created by introducing inert gas or employing a vacuum, for a time that is sufficient to recombine substantially all of the free-radicals which remain in the material from the irradiation cross-linking step, thus further cross-linking the material and stabilizing it to oxidation. Thermal distortion of the preform material during heat treatment may occur without affecting the final implant since the implant is formed from the preform after heat treatment. This allows higher temperatures to be used than would be possible in processes where the finished implants are heat treated. The hold time required for reaction of the free radicals decreases with increasing temperature. Thus, a wide range of temperatures, including temperatures above the melting point of the UHMWPE, is acceptable in the heat treatment step of the current invention.

The irradiated preform preferably is heated at a temperature at or above the onset of melting temperature of the irradiated heat-treated preform material, and preferably at a temperature near or above the peak melting temperature of the irradiated heat-treated polymer for a time of 2–120 hours, preferably 5–60 hours, more preferably 12–60 hours. The onset of melting temperature is defined herein as the temperature at the intersection of the baseline and steepest negative slope of the DSC melting endotherm. The baseline intersects the initial portion of the melting endotherm and is tangent to the final portion of the curve. The peak melting temperature is defined herein as the location of the peak of the melting endotherm. The onset of melting temperature for irradiated, heat-treated UHMWPE is generally about 120° C. and the peak melting temperature is generally between 135° C. and 140° C. An especially preferred embodiment of the current invention is irradiation with a dose of 1.5–6 Mrads followed by heat treatment at 150–170° C. for a period of 6–60 hours, more preferably 12–60 hours. The temperature and hold time that is sufficient to react substantially all of the free-radicals may be determined by measuring the oxidation of the samples using the method described below. Preferably, the temperature and hold time are chosen such that oxidation levels of less than about 0.2 carbonyl area/mil sample thickness, preferably less than about 0.1 carbonyl area/mil sample thickness, after aging as measured by this method are obtained. Heat treatment at or above the onset of melting temperature results in improved molecular mobility and elimination of free radicals in the crystalline regions of the polymer and increased cross-linking and reduced oxidation in aged samples. When heat treatment is carried out at lower temperatures, elimination of free radicals is less complete resulting in higher levels of residual oxidation upon aging.

Standard UHMWPE may be irradiated and pressure recrystallized to convert the UHMWPE into an extended chain conformation by conducting the heat treatment step using the temperatures and pressures disclosed for pressure recrystallization in U.S. Pat. No. 5,478,906. In pressure recrystallizing UHMWPE, the polymer is placed in a pressure vessel in water and enough pressure to withstand the pressure the water will develop at the operating temperatures. The temperature of the vessel is raised to melt the polyethylene which generally melts at 135–150° C. at one atmosphere, and about 200° C. at 50,000 psi. The time required to melt the polymer depends on the size of the UHMWPE preform used. Because UHMWPE is a poor heat conductor and has a very high heat of crystallization, it can take 1–2 hours to heat a 3 in. diameter rod to 200° C. with the vessel at 220° C. Once the polymer is hot and molten, the pressure is applied. Preferred pressures are about 33 kpsi (230 MPa) to 70 kpsi (480 MPa). Further improvement in properties may be achieved by annealing the UHMWPE in an inert atmosphere at temperatures above the melting point prior to pressure recrystallization. Pressures of greater than 45 kpsi (310 MPa) are preferred for pressure recrystallization of material which is pre-annealed prior to pressure recrystallization. The cooling time normally is about 6 hours from 250° C. to 75° C., but forced cooling of the vessel can reduce this to 1–2 hours with no adverse effects on the product.

Preferably, the UHMWPE material prepared according to the process of the current invention is an isotropic material, with no significant molecular or crystalline orientation. In order to prevent inducing residual stress in the polymer, thermal treatment after irradiation is preferably performed in such a manner that no non-uniform forces which could lead to deformation of the material during heat treatment will occur. During heat treatment the preform can be subjected to uniform pressure, such as isostatic or hydrostatic pressure, or alternatively, the preform can be heated in the absence of any externally applied pressure, so as to not deform the UHMWPE. It is undesirable to deform the preform by application of compressive or other forces as this results in an oriented material which may deform due to internal stresses after machining of the implant.

After a predetermined time, the cross-linked preform is cooled while still in an inert atmosphere or vacuum. The cross-linked preform is cooled to a temperature less than about 100° C., preferably less than about 50° C., more preferably to room temperature, prior to exposing the preform to air. If the preform was packaged during the heat treatment step, after cooling it is removed from the packaging and formed into an implant using methods known in the art such as machining. The cross-linked UHMWPE is especially useful as a bearing surface, for example in prosthetic hip joint cups and as other prosthetic shapes for replacement of other joints of the human body, including knees, shoulders, fingers, spine, and elbows. The finished implant is then packaged and sterilized using non-radical-forming methods. Because the implant is oxidatively stabilized, it is not necessary to package the finished implant in an inert atmosphere. For example, the implant can be packaged in air-permeable packaging and sterilized using gas plasma or ethylene oxide methods which are known in the art. For example a PLAZLYTE® gas plasma sterilization unit, manufactured by Abtox (Mundelein, Ill.), may be used.

In an alternate embodiment of the current invention, the UHMWPE preform is pre-annealed prior to the irradiation step. In the pre-annealing step, the preform is subjected to a temperature of 280° C.–355° C., preferably 320° C.–355° C., for at least 0.5 hour, preferably at least 3 hours, in an inert atmosphere, without the application of external pressure. It is generally desirable to heat the polymer as close as possible to, without reaching, its decomposition temperature. The pre-annealed preform is then cooled non-precipitously to a temperature of about 130° C. or below, the rate of cooling being such that temperature gradients producing internal stresses in the article are substantially avoided. Rapid cooling, such as by immersion in cold water, should be avoided as it causes internal voids to form. It is generally convenient to allow the polymer to cool wrapped in insulation. The pre-annealed preform has improved elongation, impact resistance, and crystallinity over the starting UHMWPE. The cooled pre-annealed preform is then irradiated and annealed as described above.

TEST METHODS

Unless noted otherwise, test specimens were prepared from the interior of the preform rods.

Type IV tensile specimens comforming to ASTM D-638 were machined from the UHMWPE sample materials. The test specimens were mounted in a Lloyd LR10K mechanical test frame and tested for the tensile yield stress (TYS), ultimate tensile stress (UTS) and percent elongation according to ASTM D-638. Type IV specimens were used to measure UTS, TYS, and percent elongation for Examples 1–27, and Comparative Examples A–C.

Type I tensile specimens were machined from the UHMWPE samples and mounted in the test frame. Tensile modulus was measured on these samples according to ASTM D-638. Type I tensile specimens were also used to measure TYS, UTS and percent elongation for Examples 28–37 and Comparative Example D.

All tensile properties represent the average of 5 test specimens.

Thermal analysis was performed on disks approximately 3 mm thick and 1.5 mm in diameter which were cut from the UHMWPE sample rod. The disk was placed in a differential scanning calorimetry (DSC) sample pan and weighed. The lid was placed on the pan and crimped in place. The pan was placed in a DuPont Model 2000 thermal analyzer and allowed to equilibrate at a temperature of 50° C. It was then heated at a rate of 20 degrees C./minute. The peak melting point was taken as the location of the peak of the melting endotherm. The onset of melting temperature was determined from the DSC curve as the intersection of the baseline and the steepest negative slope of the melting endotherm. The baseline intersects the initial portion of the melting endotherm and is tangent to the final portion of the curve. The heat of fusion (Hf) was calculated as the area of the melting endotherm.

The percent crystallinity was determined by dividing the measured heat of fusion by the theoretical heat of fusion of crystalline UHMWPB, 290 J/g.

Density measurements were performed on 1.5 mm thick disks of UHMWPE cut from the UHMWPE sample rods. The disks were soaked in a 65/35 solution by weight of 2-propanol, histological grade, and water. The sample was placed into a calibrated density gradient column. The density was determined from the equilibrium position of the sample in the column and is reported as g/cc.

Resistance to deformation (creep) was measured in accordance with ASTM D-621 with the following modifications: samples machined into cylinders or cubes without the use of lubricating liquids; samples measured 0.5 in.×0.5 in. ×0.5 in.

Impact resistance was measured using the notched Izod test given in ASTM D-256 with the following modifications: samples machined into shape without the use of lubricating liquid; type A or notched IZOD; specimen size was 0.5 in.×2.5 in.; 0.4 in. from bottom of vertex to opposite side; 1.25 in. impacted end (from end of bar to vertex of notch); the notch should be the specified angle of 22.5 degrees. Impact strength was also measured using double notched Izod specimens and the test method described in ASTM F-648 Annex A1.

Oxidative aging was performed on specimens which were wrapped in porous breather fabric to prevent close packing of the specimens and allow free gas access to all surfaces. The specimens were then loaded into a 4 in.×8 in. cylindrical pressure bomb and sealed. The bomb was pressurized to 5 atmospheres (73.5 psi) with oxygen and heated with cylindrical band heaters to 70° C. and held for 14 days. Aged wear test results were obtained by aging the hip cups using this procedure prior to wear testing. Similarly, aged Izod specimens for double notch impact strength measurements were prepared according to ASTM F-648 Annex A1 followed by oxidative aging prior to strength measurements.

Specimens for oxidation measurements were cut from the interior of the cooled preform rods after gamma-irradiation and annealing. The samples were 45 degree wedge cuts from 0.5 inch thick by 2.5 inch diameter disks. Oxidation measurements were made on 250 micron thick sections prepared by cutting the wedge-shaped specimens through their thickness using a band saw. A 250 micron thick slice was microtomed off the freshly exposed surface and analyzed using FTIR. Aged oxidation results were obtained from wedge cuts that were aged according to the oxidative aging procedure described above prior to preparing the 250 micron thick section. The sample was mounted in a Digilab FTIR fitted with a microscope with a motorized stage. The FTIR aperture was focused through the microscope to allow measurement of the infrared absorbance in a small (25 micron×200 micron) section of the sample. The microscope stage was moved by a stepper motor in increments of 50 microns to measure the carbonyl absorbance at a number of locations from the surface down to a depth of 4 mm. Oxidation was quantified based on the absorbance of the carbonyl peaks at 1670–1730 wavenumbers as compared to a reference peak corresponding to methylene stretching along the polymer backbone at 4250 wavenumber using the method of Nagy & Li, A Fourier Transform Infrared Technique For The Evaluation of Polyethylene Bearing Materials, Transactions, 16th Annual Meeting, The Society for Biomaterials, 3:109, 1990. An average oxidation level was calculated by integrating the carbonyl concentration versus depth curve to a depth of 2.05 mm. Oxidation is reported as carbonyl area/mil sample thickness.

Swell ratios were measured per ASTM D 2765 method C. The test specimens were 0.32 inch cubes. All swell ratios represent the average of 4 test specimens.

Gas plasma sterilization was performed by (a) placing the component in a breathable pouch and heat sealing, (b) placing the packaged components in the chamber of a PLAZLYTE® Sterilization System (Abtox, Inc., Mundelein, Ill.) and (c) filling the chamber with peracetic acid vapor and holding for a predetermined time, (d) evacuting the chamber, (e) filling the chamber with a filtered secondary plasma and holding for a predetermined time, (f) evacuating the chamber, (g) repeating steps (c)–(f), (h) filling the chamber with atmospheric air, (i) evacuating the chamber, and (j) repeating steps (h) and (i) to complete the cycle.

Wear rates were obtained by mounting test hip cups having a 28 mm spherical hole in the cup in a hip simulating wear tester which included 28 mm diameter femoral heads. The test cups were machined from the interior of the preform rods and were pre-soaked for 30 days in bovine calf serum solution containing 20 mM EDTA and 0.2 wt % sodium azide. The cups were sterilized by gas plasma prior to wear testing. The wear tester simulated the human gait using the Paul hip curve at a 1900 N peak load and a frequency of 1.1 Hz. The load is applied in the vertical direction. The test cup in the hip simulator is immersed in bovine calf serum and angled at 23 degrees from the horizontal. Every 500,000 cycles, the cups are washed, dried and weighed. Each test was run between 2.5 and 5 million cycles. Soak controls cups were used to correct for fluid absorption. The wear rate is the soak corrected change in cup weight per million cycles.

EXAMPLES

In each of Examples 1–3, 28–37, and Comparative Examples A–D, the UHMWPE preform comprised GUR 4150 HP ram-extruded UHMWPE (PolyHi Solidur, Fort Wayne, Ind.) in the form of 3.5 in. (8.9 cm) diameter rods approximately 30 in. (76.2 cm) in length. This polymer has a molecular weight of approximately 6 million, a peak melting point of about 135° C., and a percentage crystallinity of about 45–55%.

Examples 1–3

Rods of UHMWPE as described above were placed in separate pouches of heat sealable packaging foil having a MYLAR® polyester coating, SP Class E style 1.40 sleevestock (Shield Pack, Inc., West Monroe, La.), flushed with nitrogen and then evacuated. This procedure was repeated and the pouches were then sealed under vacuum. The rod of Example 1 was irradiated with a dose of 1 Mrad of gamma irradiation from a Cobalt-60 source. Gamma irradiation was performed by Isomedix (Morton Grove, Ill.). The rods of Examples 2 and 3 were irradiated with doses of 2.5 Mrads and 5 Mrads, respectively. After irradiation, the packaged rods were placed individually in an oven at a temperature of 325° C. and held at that temperature for 4.5 hours. At the end of 4.5 hours, the rods were cooled in the oven at about 20° C./hr to ambient temperature in their packages. The cooled rods were then removed from their packages and mechanical and physical properties and oxidation were measured as described above. The results and process conditions are shown in Table I. These examples show excellent oxidation resistance under both aged and unaged conditions compared to Comparative Examples A, B, and C. The effect is greatest for Example 3 (vs. Comparative Example C) which was irradiated at the higher dose of 5 Mrads. Aged and unaged oxidation resistance for Examples 1–3 is comparable to unirradiated Example D. This improved performance is due to the substantially complete quenching of the free radicals by annealing at 325° C. These examples also shown an unexpected benefit of a large increase, approximately 2×, in the % elongation to break, attributed to the temperature of the annealing. Elongation generally increases significantly for samples which are annealed or pre-annealed at temperatures of greater than about 280° C.

Comparative Examples A–C

UHMWPE rods for comparative Examples A and C were packaged under vacuum as described in Examples 1–3, and irradiated at doses of 1 Mrad and 5.0 Mrad, respectively. The rod of Comparative Example B was irradiated with 2.5 Mrad in air without packaging. The rods were not heat-treated after irradiation. Mechanical and physical properties and oxidation were measured as described above. The results and process conditions are shown in Table I. Test specimens were taken from the interior of the rod, thus substantially eliminating any effects of oxidation in comparative Example B which was irradiated in air. For Example B, an unaged wear rate of 15 mg/million cycles and an aged wear rate of 88 mg/million cycles were measured after 5 million cycles. These examples show oxidative degradation in the accelerated aged state, demonstrating the reaction of unquenched free radicals with oxygen. Example B also shows the effect of this oxidation on impact strength and wear. Impact strength is reduced by a factor of 10 after aging. Although the unaged wear rate for Example B is improved compared to Comparative Example D, the wear rate is increased by nearly 6× after aging, significantly higher than the wear rate for Comparative Example D.

Comparative Example D

The UHMWPE rods for this example were not irradiated, heat treated or pressurized. They were gas plasma sterilized by a PLAZLYTE® Sterilization System (Abtox Inc., Mundelein, Ill.). The mechanical and physical properties are similar to commercially available UHMWPE rods and are shown in Table V. An unaged wear rate of 30 mg/million cycles and an aged wear rate of 33 mg/million cycles were obtained after 5 million cycles.

Examples 4–15

Hoechst GUR 415 UHMWPE in the form of 3 in. (7.6 cm) diameter rods obtained from PolyHi Solidur were cut to about 15 in. (38.1 cm) length and sealed in polyethylene lined aluminum foil bags under a nitrogen atmosphere.

The rods were irradiated with Co-60 gamma rays and aged for one month in the sealed bags to permit the free radicals to react. Irradiation doses of 0.5, 1, 2, and 5 Mrad were used. The bars were then removed from the bags and immediately placed in a pressure vessel, as described in Simmons et al. U.S. Pat. No. 5,236,669, which patent is hereby incorporated by reference. Pressure recrystallization was conducted by sealing the vessel and pressurizing with water to about 5000 psi. The vessel was then heated over a period of 1.5 hours to 250° C. After 2 hours, the pressure was raised to 50,000 psi and maintained there for the rest of the pressure treatment. After 1 to 2 hours at 250° C., the vessel was allowed to cool to 75° C. at which point the pressure was released and the product recovered. Additional rods were also pressure recrystallized using the above procedure at 39,000 and 34,000 psi. The results are shown in Table II.

Examples 16–21

In these examples, the 3 in. diameter GUR 415 UHMWPE rods were pre-annealed at 325° C. for 4.5 hours in nitrogen, cooled in nitrogen at approximately 20° C./hr, and then sealed in aluminum foil/polyethylene bags under nitrogen. The bars were then irradiated with gamma rays. After aging one month, the polymers were pressure recrystallized as described above. Process conditions and results are given in Table III. The polymer was converted to extended chain form only at higher pressure. The samples treated with 50,000 psi during pressure recrystallization had higher melting points, higher heats of fusion, higher tensile moduli, higher maximum strengths, higher tensile strength at yield, higher Izod impact strength, and improved creep resistance.

The pre-annealed samples of Examples 16–21 have higher elongations than the corresponding samples of Examples 4, 5, 7, 8, 10 and 11 which were not pre-annealed.

Examples 22–23

In these examples, 3 in. diameter GUR 415 UHMWPE rods were gamma irradiated at 2.5 Mrad and 5.0 Mrad in nitrogen and pressure recrystallized at 39,500 psi using the process described in Examples 4–15. Irradiation conditions and results are given in Table IV.

Examples 24–25

In these examples, 3 in. diameter GUR 415 UHMWPE rods were gamma irradiated at 2.5 Mrad and 5 Mrad, and then subjected to pressure recrystallization at 33,500 psi using the process described in Examples 4–15. Irradiation conditions and results are given in Table IV.

Examples 22–23 and 24–25 show excellent oxidation resistance in both the aged and unaged states as did Examples 1–3, also due to substantially complete quenching of free radicals during the pressure recrystallization step. The samples also show increased crystallinity, which in turn shows that it is possible to change the crystal structure of the polymer even in the presence of crosslinks.

Examples 26–27

In these examples, 3 in. diameter GUR 415 UHMWPE rods were pre-annealed in nitrogen at 325° C. for 4.5 hours prior to gamma irradiation, cooled at approximately 20° C./hr, followed by gamma irradiation under nitrogen at 2.5 Mrad and 5 Mrad, and then subjected to pressure recrystallization at 39,500 psi using the process described in Examples 4–15. Irradiation conditions and results are given in Table IV. These examples show that by combining a pre-annealing step (325° C.) with pressure recrystallization after irradiation, oxidation resistance is maintained, the elongation is increased and the crystallinity increased compared to conventional UHMWPE (Comparative Example D).

Example 28–30

UHMWPE rods 28–30 were packaged and processed as described in Example 2 (2.5 Mrad) except that the rods were heated at 155° C. for 6, 24, and 48 hours respectively, removed from the oven and cooled. The process conditions, mechanical and physical properties are shown in Table V. These examples show that annealing at 155° C. creates a material with excellent oxidation resistance. Irradiated samples 28–30 exhibited a reduction in double notched Izod compared to the unirradiated Comparative Example D. It also shows that the crosslinking produced by the 2.5 Mrad radiation dose yields a swell ratio of 3.9 as compared to 24.1 for Example D. An unaged wear rate of 14 mg/million cycles was measured after 5 million cycles for hip cups prepared from the cross-linked polymer of Example 30.

Examples 31–33

UHMWPE rods 31, 32 and 33 were packaged and processed as described in Example 3 (5 Mrad) except that the rods were heated to 155° C. for 6, 24 and 48 hours respectively, removed from the oven, and cooled. The process conditions, mechanical and physical properties are shown in Table V. These examples show that UHMWPE exposed to 5 Mrads of gamma irradition then annealed at 155° C. also gives excellent oxidation resistance. It also shows that the radiation dose reduces the impact strength and the elongation. A comparison of these swell ratios, 2.6, with Examples 28–30 and D, show that crosslinking is increased with radiation dose. An unaged wear rate of 0.8 mg/million cycle and an aged wear rate of 0.6 mg/million cycles were measured for Example 32 after 2.5 million cycles. The wear rate of Example 32 is greatly reduced compared to Examples 30, B and D. By performing both the irradiation and annealing steps, the wear and oxidation resistance of this material is greatly improved over material that is irradiated but not annealed. Oxidation resistance is comparable to unirradiated polymer (Comparative Example D) and wear performance is significantly improved.

Example 34–36

UHMWPE rods 34, 35 and 36 were packaged and processed as described in Example 3 (5 Mrad) except that the rods were heated to 200° C. for 6, 24 and 48 hours respectively, removed from the oven and cooled. The process conditions, mechanical and physical properties are shown in Table V. These examples show that annealing at 200° C. is also effective for producing an oxidation resistant material.

Example 37

This rod was packaged and processed as described in Example 3 (5 Mrad) except the rod was heated to 120° C. for 48 hours, removed from the oven, and cooled. An unaged wear rate of 5 mg/million cycles was measured after 5 million cycles. Results are shown in Table V. This example shows the improved wear resistance of a material crosslinked at 5 Mrads and annealed at 120° C. for 48 hours as compared to Examples 30 (2.5 Mrad, 1 55° C./48 hrs), C (5 Mrad, unannealed), and D (unirradiated).

TABLE I

| Example | 1 | 2 | 3 | A | B | C | D |
|---|---|---|---|---|---|---|---|
| Gamma dose (Mrad) | 1 | 2.5 | 5 | 1 | 2.5 | 5 | 0 |
| Hold Temp/Time (deg C./hr) | 325/4.5 | 325/4.5 | 325/4.5 | none | none | none | none |
| Mechanical Properties | | | | | | | |
| Type I Samples | | | | | | | |
| Modulus (kpsi) | 147.8 | 148.5 | 144.3 | | 143.1 | | 137.0 |
| Secant Modulus (kpsi) | | | | 122.3 | | | |
| Type IV Samples | | | | | | | |
| TYS | 3.544 | 3.454 | 3.429 | 3.553 | 3.507 | 3.669 | 3.396 (Type I) |
| UTS | 5.603 | 5.481 | 5.644 | 5.324 | 5.47 | 5.511 | 5.152 (Type I) |
| % Elongation | 805 | 700 | 613 | 310 | 340 | 267 | 343 (Type I) |
| Impact Strength - Double Notched Izod (Ft-lb/sq in) | | | | | | | |
| (unaged) | | | | | 48.1 | | 48.1 |
| (aged) | | | | | 4.8 | | |
| Physical Properties | | | | | | | |
| Density (g/cc) | 0.9461 | 0.9442 | 0.9409 | 0.9356 | 0.9378 | 0.9379 | .9344 |
| Hf(J/g) | 170.9 | 184.2 | 161.6 | 145 | 163.3 | 165.8 | |
| % Crystallinity | 58 | 63 | 55 | 50 | 56 | 57 | 51 |
| Peak Tm (°C.) | 138.1 | 137.1 | 135.6 | 139.4 | 138.7 | 137.4 | 136.7 |
| Onset of melting T (°C.) | 126.0 | 125.8 | 123.0 | | 127.2 | | 130.8 |
| Oxidation(unaged) | 0.067 | 0.048 | 0.068 | 0.154 | 0.172 | 0.398 | .054 |
| oxidation(aged) | 0.14 | 0.078 | 0.117 | 0.527 | 1.107 | 2.78 | .075 |
| Swell Ratio | | | | | | | 24.1 |
| Wear Rate (mg/million cycles) | | | | | | | |
| (unaged) | | | | | 15 | | 30 |
| (aged) | | | | | 88 | | 33 |

| Example | 4 | 5 | 6 | 7 | 8 | 9 | 10 | 11 | 12 | 13 | 14 | 15 |
|---|---|---|---|---|---|---|---|---|---|---|---|---|
| Gamma Dose (Mrad) | 0.5 | 0.5 | 0.5 | 1 | 1 | 1 | 2 | 2 | 2 | 5 | 5 | 5 |
| Pressure (kpsi) | 50 | 39 | 34 | 50 | 39 | 34 | 50 | 39 | 34 | 50 | 39 | 34 |
| Tensile Strength, psi | | | | | | | | | | | | |
| Yield | 3877 | 3668 | 3504 | 3804 | 3543 | 3470 | 3597 | 3524 | 3446 | 3628 | 3553 | 3394 |
| Max | 5871 | 6400 | 5936 | 6662 | 6463 | 5514 | 6551 | 5517 | 5047 | 5766 | 5205 | 5155 |
| Break | 5629 | 6397 | 4791 | 6570 | 5759 | 4995 | 6054 | 4462 | 5023 | 4877 | 5204 | 4220 |
| Modulus (kpsi) | 288.4 | 272.8 | 229.3 | 248.3 | 239.0 | 227.8 | 309.1 | 250.3 | 292.4 | 237.7 | 234.1 | 188.1 |
| Elongation, % | | | | | | | | | | | | |
| Yield | 7.5 | 7.5 | 7.5 | 7.5 | 7.5 | 7.5 | 7.5 | 7.5 | 7.5 | 7.5 | 7.5 | 7.5 |
| Break | 290 | 309 | 232 | 296 | 324 | 311 | 272.7 | 289.5 | 286.3 | 243 | 247 | 254 |
| IZOD ft lb/in of notch | 19.6 | 20.1 | 19.8 | 19.7 | 19.6 | 19.1 | 19.8 | 19.8 | 18.7 | 19.4 | 17.4 | 17.9 |

-continued

| Example | 4 | 5 | 6 | 7 | 8 | 9 | 10 | 11 | 12 | 13 | 14 | 15 |
|---|---|---|---|---|---|---|---|---|---|---|---|---|
| Deformation (%) 24 hrs., 23 deg. C., 1000 psi. | 1.0 | 1.5 | 1.6 | 1.6 | 1.7 | 1.9 | 1.7 | 1.7 | 1.9 | 1.8 | 1.9 | 1.8 |
| DSC |  |  |  |  |  |  |  |  |  |  |  |  |
| Peak mp, deg. C. | 147.6 | 144.8 | 138.3 | 147.6 | 147.3 | 137.2 | 150.4 | 150.4 | 145.5 | 146.0 | 145.7 | 147.7 |
| Hf(J/g) | 185.7 | 170.4 | 133.7 | 185.7 | 173.6 | 53.7 | 171.3 | 171.3 | 170.4 | 178.5 | 183.9 | 187.2 |
| Peak mp, deg C.* | S | S | 145 | S | S | 143.9 | S | S |  |  | S | S |
| Hf(J/g) |  |  | 58.4 |  |  | 125.2 |  |  |  |  |  |  |

(*S stands for shoulder on low temperature side of DSC curve)

TABLE III

Physical Properties of Pre-Annealed (325° C.) UHMWPE, Gamma Irradiated and Pressure Recrystallized

| Example | 16 | 17 | 18 | 19 | 20 | 21 |
|---|---|---|---|---|---|---|
| Dose (Mrad) | 0.5 | 0.5 | 1 | 1 | 2 | 2 |
| Pressure (kpsi) | 50 | 39 | 50 | 39 | 50 | 39 |
| Tensile Strength, psi |  |  |  |  |  |  |
| Yield | 4277 | 3773 | 4066 | 3543 | 4051 | 3594 |
| Max | 5289 | 4696 | 5145 | 4332 | 5142 | 4119 |
| Break | 4532 | 4695 | 4582 | 4331 | 4604 | 4117 |
| Modulus (kpsi) | 335.2 | 276.0 | 296.9 | 219.0 | 293.6 | 266.5 |
| Elongation, % |  |  |  |  |  |  |
| Yield | 5 | 7.5 | 5 | 7.5 |  | 7.5 |
| Break | >432 | >500 | >450 | 417 | >400 | 388 |
| IZOD (ft lb/in of notch) | 24.0 | 20.5 | 24.2 | 21.6 | 23.6 | 21.9 |
| Deformation (%) 24 hrs, 23 deg C., 1000 psi | 0.7 | 2.8 | 0.8 | 1.8 | 1.2 | 2.3 |
| DSC |  |  |  |  |  |  |
| mp, deg C. | 148.8 | 140.7 | 148.9 | 140.8 | 148.6 | 140.8 |
| Hf (J/g) | 217 | 175 | 207 | 185.9 | 202.8 | 177.9 |

TABLE IV

| Example | 22 | 23 | 24 | 25 | 26 | 27 |
|---|---|---|---|---|---|---|
| Gamma dose (Mrad) | 2.5 | 5 | 2.5 | 5 | 2.5 | 5 |
| Pre-annealing Heat/hold time (deg C./hrs) | none | none | none | none | 325/4.5 | 325/4.5 |
| Pressure (psi) | 39,500 | 39,500 | 33,500 | 33,500 | 39,500 | 39,500 |
| MECHANICAL PROPERTIES |  |  |  |  |  |  |
| Type I Samples |  |  |  |  |  |  |
| modulus (kpsi) | 172.6 | 171.5 | 153.7 | 151.2 | 144.3 | 187.5 |
| Secant modulus (kpsi) | 157 | 146.9 | 136.8 | 136.7 | 178.9 | 162.1 |
| Type IV Samples |  |  |  |  |  |  |
| TYS (kpsi) | 3.565 | 3.591 | 3.423 | 3.508 | 3.926 | 3.901 |
| UTS (kpsi) | 5.855 | 5.862 | 5.439 | 5.475 | 5.696 | 5.57 |
| % Elongation | 287 | 258 | 292 | 256 | 525 | 568 |
| PHYSICAL PROPERTIES |  |  |  |  |  |  |
| Density (g/cc) | 0.9393 | 0.9396 | 0.9368 | 0.9381 | 0.9475 | 0.9461 |
| Hf (J/g) | 188.7 | 158.1 | 150.8 | 174.4 | 177.4 | 176.7 |
| % Crystallinity | 65.069 | 54.517 | 52 | 60.138 | 61.172 | 60.931 |
| Tm (deg C.) | 143.5 | 143.8 | 143.1 | 143.5 | 134.7 | 136.3 |
| oxidation (unaged) | 0.055 | 0.082 | 0.092 | 0.074 | 0.082 | 0.065 |
| oxidation (aged) | 0.08 | 0.082 | 0.08 | 0.096 | 0.133 | 0.16 |

TABLE V

| Example | 28 | 29 | 30 | 31 | 32 | 33 | 34 | 35 | 36 | 37 |
|---|---|---|---|---|---|---|---|---|---|---|
| Gamma dose (Mrad) | 2.5 | 2.5 | 2.5 | 5 | 5 | 5 | 5 | 5 | 5 | 5 |
| Heat/hold time (°C./hrs) | 155/6 | 155/24 | 155/48 | 155/6 | 155/24 | 155/48 | 200/6 | 200/24 | 200/48 | 120/48 |
| MECHANICAL PROPERTIES |  |  |  |  |  |  |  |  |  |  |
| Type I Tensile Samples |  |  |  |  |  |  |  |  |  |  |
| Modulus (kpsi) |  | 115.7 | 114.3 | 124.9 | 111.9 | 116.2 | 110.8 | 112.4 | 118.4 | 108.7 |
| Secant mod. (kpsi) |  | 106.5 | 104.6 | 114.3 | 99.3 | 104.9 | 101.8 | 100.6 | 109.6 | 98.5 |
| TYS (kpsi) |  | 3.080 | 3.100 | 3.056 | 3.068 | 3.147 | 3.113 | 3.075 | 3.115 | 3.094 |
| UTS (kpsi) |  | 5.130 | 5.436 | 5.024 | 5.037 | 5.238 | 5.267 | 4.698 | 5.053 | 5.000 |
| % Elongation |  | 331 | 326 | 321 | 272 | 273 | 283 | 265 | 263 | 278 |
| Impact Strength, Double Notch (ft lb/in$^2$) |  |  |  |  |  |  |  |  |  |  |
| (unaged) |  | 44.0 | 44.7 | 44.0 | 36.2 | 35.1 | 37.3 | 37.3 | 38.3 | 36.9 |
| (aged) |  | 44.0 | 44.6 | 42.7 | 36.0 | 35.7 | 37.8 | 37.0 | 36.8 | 37.1 |
| Deformation (%) (24 hrs, 23 °C., 1 kpsi) |  | 1.5 | 1.1 | 1.4 | 1.2 | 1.6 | 1.0 | 1.0 | 1.2 | 1.2 |

TABLE V-continued

| Example | 28 | 29 | 30 | 31 | 32 | 33 | 34 | 35 | 36 | 37 |
|---|---|---|---|---|---|---|---|---|---|---|
| PHYSICAL PROPERTIES | | | | | | | | | | |
| Density (g/cc) | 0.9292 | .9289 | .9298 | .9295 | .9299 | .9292 | .9292 | .9295 | .9285 | |
| Hf(J/g) | 135.6 | 146.3 | 132.5 | 141.2 | 128.5 | 147.4 | 131.4 | 142.9 | 145.8 | |
| % Crystallinity | 47 | 50 | 45 | 49 | 44 | 51 | 45 | 49 | 50 | |
| Peak Tm (°C.) | 134.7 | 134.4 | 135.1 | 137.8 | 136.6 | 134.9 | 134.8 | 137.3 | 135.8 | |
| Onset of melting T, (°C.) | 121.8 | 123.6 | 122.7 | 121.3 | 120.9 | 120.1 | 119.9 | 121.8 | 120.5 | |
| oxidation | | | | | | | | | | |
| (unaged) | .067 | .052 | 0.064 | 0.052 | 0.053 | 0.065 | 0.065 | 0.055 | 0.110 | |
| (aged) | .059 | .057 | 0.076 | 0.069 | 0.064 | 0.081 | 0.074 | 0.140 | 0.082 | |
| Swell ratio | 3.9 | 3.3 | 3.7 | 2.5 | 2.6 | 2.6 | 2.8 | 2.4 | 2.7 | |
| Wear rate(mg/million cycles) | | | | | | | | | | |
| (unaged) | | | 14 | | 0.8 | | | | | 5 |
| (aged) | | | | | 0.6 | | | | | |

We claim:

1. A process for preparing a medical implant having an improved balance of wear properties and oxidation resistance comprising the steps of:
   irradiating a preform of ultrahigh molecular weight polyethylene to form free radicals;
   annealing the irradiated preform by heating in a substantially oxygen-free atmosphere at a temperature above about 150° C. for a time sufficient to recombine substantially all of the free radicals and cross-link the ultrahigh molecular weight polyethylene;
   cooling the cross-linked preform while maintaining a substantially oxygen-free atmosphere;
   forming a medical implant from the cross-linked preform;
   packaging the medical implant in an air-permeable package; and
   sterilizing the packaged implant using non-irradiative methods.

2. The process of claim 1 wherein the irradiating step comprises irradiating the preform with gamma radiation at a dose of 0.5–10 Mrad.

3. The process of claim 1 wherein the irradiating step comprises irradiating the preform with gamma radiation at a dose of 1.5–6 Mrad.

4. The process of claims 2 or 3 wherein the preform is contained in an inert atmosphere or vacuum during the irradiating step.

5. The process of claim 1 wherein the implant is sterilized using a gas plasma.

6. The process of claim 1 wherein the implant is sterilized using ethylene oxide.

7. The process of claim 1 wherein the annealing step is performed near or above the peak melting temperature.

8. The process of claim 1 wherein the annealing step is performed at a temperature greater than about 160° C.

9. The process of claim 1 wherein the annealing step is performed at a temperature of 150–170° C. for 12–60 hours.

10. The process of claim 1 wherein the annealing step is performed for a time sufficient to form a cross-linked preform having an oxidation level of less than 0.2 carbonyl area/mil sample thickness after aging the cross-linked preform at 70° C. for 14 days in oxygen at a pressure of about 5 atmospheres.

11. The process of claim 8 wherein the preform is irradiated with a dose of 1.5–6 Mrads and the irradiated preform is annealed at a temperature of 150–170° C. for a period of 12–60 hours.

12. The process of claim 1 wherein the annealing step comprises melting the irradiated preform and applying an isostatic or hydrostatic pressure of 33–70 kpsi.

13. The process of claim 1 further comprising pre-annealing the preform at a temperature of 280° C.–355° C. in an inert atmosphere without the application of external pressure for at least 0.5 hour prior to the irradiating step.

14. The process of claim 13 wherein the preform is pre-annealed at a temperature of about 320–355° C. for at least 3 hours.

15. A process for preparing a medical implant having an improved balance of wear properties and oxidation resistance comprising the steps of:
   irradiating a preform of ultrahigh molecular weight polyethylene to form free radicals;
   annealing the irradiated preform by heating in a substantially oxygen-free atmosphere at a temperature above about 150° C. to cross-link the ultrahigh molecular weight polyethylene;
   cooling the cross-linked preform while maintaining a substantially oxygen-free atmosphere; and
   forming a medical implant from the cross-linked preform.

16. The process of claim 15 wherein the irradiating step comprises irradiating the preform with gamma radiation at a dose of 0.5–10 Mrad.

17. The process of claim 15 wherein the irradiating step comprises irradiating the preform with gamma radiation at a dose of 1.5–6 Mrad.

18. The process of claims 16 or 17 wherein the preform is contained in an inert atmosphere or vacuum during the irradiating step.

19. The process of claim 15 wherein the implant is sterilized using a gas plasma.

20. The process of claim 15 wherein the implant is sterilized using ethylene oxide.

21. The process of claim 15 wherein the annealing step is performed near or above the peak melting temperature.

22. The process of claim 15 wherein the annealing step is performed at a temperature up to about 160° C.

23. The process of claim 15 wherein the annealing step is performed at a temperature of 150–170° C. for 12–60 hours.

24. The process of claim 15 wherein the annealing step is performed for a time sufficient to form a cross-linked preform having an oxidation level of less than 0.2 carbonyl area/mil sample thickness after aging the cross-linked preform at 70° C. for 14 days in oxygen at a pressure of about 5 atmospheres.

25. The process of claim 22 wherein the preform is irradiated with a dose of 1.5–6 Mrads and the irradiated preform is annealed at a temperature of 150–170° C. for a period of 12–60 hours.

26. The process of claim 15 further comprising pre-annealing the preform at a temperature of 280° C.–355° C. in an inert atmosphere without the application of external pressure for at least 0.5 hr prior to the irradiating step.

27. The process of claim 26 wherein the preform is pre-annealed at a temperature of about 320° C.–355° C. for at least 3 hours.

28. The process of claim 15 wherein the annealing step comprises melting the irradiated preform and applying an isostatic or hydrostatic pressure of 33–70 kpsi.

29. The process of claim 15 wherein the annealing step comprises melting the preform at a temperature of 280–355° C.

30. The process of claim 29 wherein the annealing step comprises melting the preform at a temperature of 320–355° C.

31. A medical implant prepared according to the process of claims 1 or 15.

32. A cross-linked ultrahigh molecular weight polyethylene having a swell ratio of less than about 5 and an oxidation level of less than about 0.2 carbonyl area/mil sample thickness after aging the ultrahigh molecular weight polyethylene at 70° C. for 14 days in oxygen at a pressure of about 5 atmospheres.

33. The cross-linked ultrahigh molecular weight polyethylene of claim 31 having an oxidation level of less than about 0.1 carbonyl area/mil sample thickness after aging the ultrahigh molecular weight polyethylene at 70° C. for 14 days in oxygen at a pressure of about 5 atmospheres.

34. A medical implant comprising the ultrahigh molecular weight polyethylene of claims 31 or 32.

35. A process for preparing a medical implant having an improved balance of wear properties and oxidation resistance comprising the steps of:

irradiating a preform of ultrahigh molecular weight polyethylene to form free radicals;

annealing the irradiated preform by heating at a temperature above about 150° C. for a time sufficient to recombine substantially all of the free radicals and cross-link the ultrahigh molecular weight polyethylene;

cooling the cross-linked preform;

forming a medical implant from the cross-linked preform;

packaging the medical implant in an air-permeable package; and sterilizing the packaged implant using non-irradiative methods.

36. The process of claim 35 wherein the irradiating step comprises irradiating the preform with gamma radiation at a dose of about 0.5 to about 10 Mrad.

37. The process of claim 35 wherein the annealing step is performed at a temperature greater than about 160° C.

38. The process of claim 35 wherein the annealing step is performed at a temperature of 150–170° C. for 12–60 hours.

* * * * *